United States Patent [19]
Selke

[11] Patent Number: 4,956,931
[45] Date of Patent: Sep. 18, 1990

[54] IDENTIFICATION DEVICE

[75] Inventor: George V. Selke, Denver, Colo.

[73] Assignee: Clink Products, Inc., Denver, Colo.

[21] Appl. No.: 19,640

[22] Filed: Feb. 27, 1987

[51] Int. Cl.[5] ............................................. A61B 5/00
[52] U.S. Cl. ....................................... 40/633; 119/106
[58] Field of Search ..................... 40/21 R, 21 C, 304,
40/21 A, 21 B, 633; 63/3; 24/3 A, 16 PB;
119/106

[56] References Cited

U.S. PATENT DOCUMENTS

| | | | |
|---|---|---|---|
| 2,016,679 | 10/1935 | Mayer | 63/3 |
| 2,031,110 | 2/1936 | King | 63/3 |
| 3,153,869 | 10/1964 | Twentier | 40/21 C |
| 3,321,934 | 5/1967 | Boyd | 40/21 R |
| 4,031,859 | 6/1977 | Stewart | 40/21 C |
| 4,091,766 | 5/1978 | Colliard | 40/21 C |
| 4,154,011 | 5/1979 | Rakestraw et al. | 40/21 C |
| 4,318,234 | 3/1982 | Charles et al. | 40/21 C |
| 4,415,106 | 11/1983 | Connell et al. | 40/21 C |
| 4,499,680 | 2/1985 | Coburn | 40/21 C |
| 4,612,718 | 9/1986 | Golub et al. | 40/21 C |

FOREIGN PATENT DOCUMENTS

| | | | |
|---|---|---|---|
| 1047986 | 2/1979 | Canada | 24/3 A |
| 2266242 | 10/1975 | France | 40/21 C |

Primary Examiner—Gene Mancene
Assistant Examiner—Michael Lynch
Attorney, Agent, or Firm—Edna M. O'Connor; Gregory W. O'Connor

[57] ABSTRACT

An identification and personal information conveying device comprising: an elongate, flat, unitary, plastic member having a first end portion, a second end portion, and an intermediate portion and having a generally planar top surface and a generally planar bottom surface and having two parallel lateral side edges comprising a leading edge and a trailing edge and having opposite first and second end edges; information receiving and displaying assembly fixedly attached to the bottom surface of the member for receiving and displaying information particular to a wearer wearing the device; attachment assembly for attaching the first end portion of the device to the second end portion of the device for providing an annular configuration for positioning the device in encompassing relationship about a wearer's limb the top surface of the member being positioned outwardly and the bottom surface of the member being positioned inwardly whereby information provided on the information receiving and display assembly is not readily viewable without removal of the device from the wearer.

12 Claims, 2 Drawing Sheets

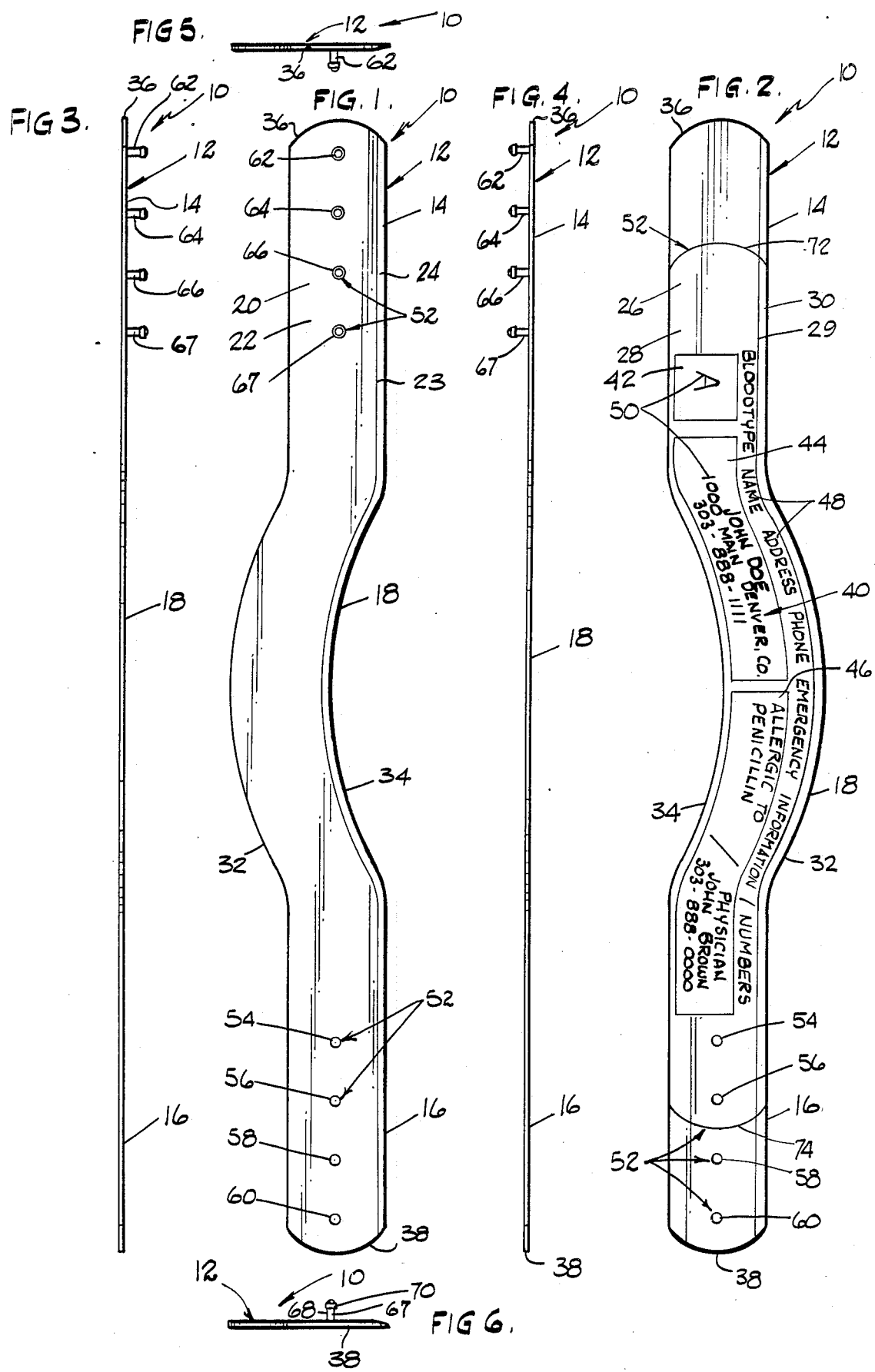

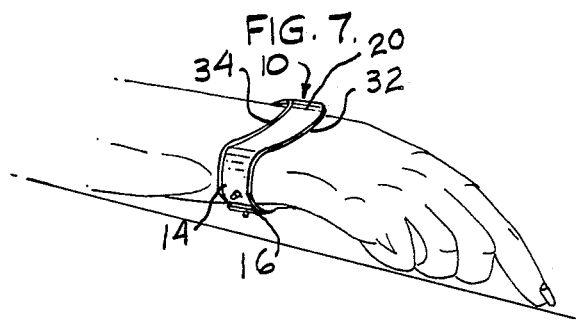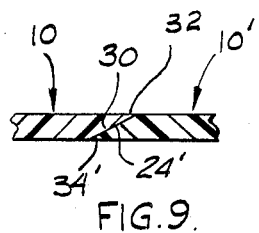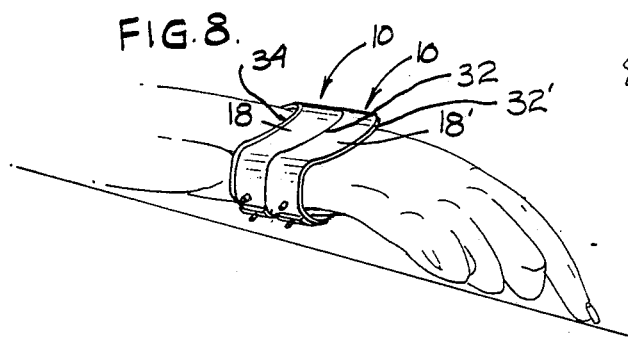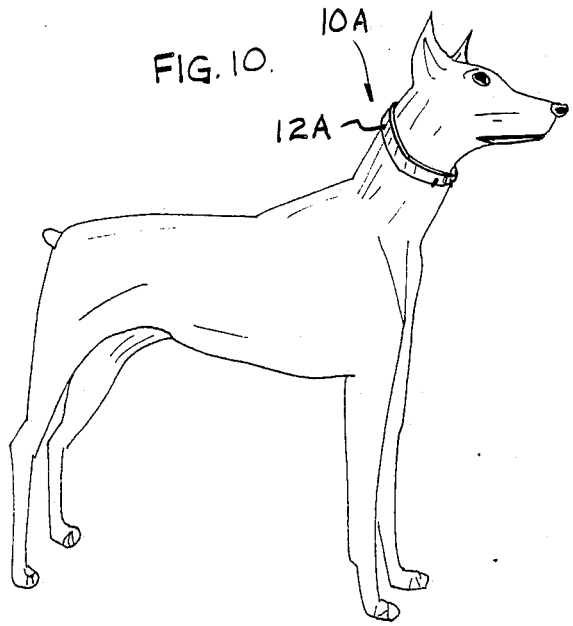

IDENTIFICATION DEVICE

BACKGROUND OF THE INVENTION

The present invention relates generally to identification devices and, more particularly, to an identification and personal information displaying device to be worn by users such as children or people engaged in sporting activities who do not ordinarily carry other forms of identification.

Identification devices are provided in many different forms. Most adult people carry information conveying documents such as driver's licenses, credit cards, etc., in their billfolds or purses. However, in certain types of activities where it is inconvenient to carry a purse or billfold, other identification devices have been employed. For example, it is customary for military personnel to wear information tags, generally referred to as "dog tags," around their neck which include identifying and medical information. Such tags are generally metal plates which have been stamped with the appropriate information for an individual. One problem with such tags for use by non-military individuals is that the tags require specialized machines to imprint the necessary identification. Such machines are not generally available, and thus, a person wishing to purchase such identification tags must generally wait a considerable period of time, often several weeks, before receiving the tags because of the need to send information to be provided on a tag to the manufacturer for stamping. Another drawback to the use of such identification tags is that, when more than one tag is used, the tags tend to rattle against one another. A further drawback of such tags is that they must be worn about the neck and are generally unattractive when exposed to view. As a result of the many inconveniences associated with military-type tags, such tags are not in common use outside of the military. However, a need for such identification devices clearly exists for persons such as joggers or persons engaged in other athletic activities who find it inconvenient to carry a billfold, etc., and yet who may need to be quickly identified in an emergency medical situation. A need for an identification device is also readily apparent for children, who do not generally carry billfolds, etc., and who may themselves have trouble conveying necessary identification or medical information, especially in emergency situations. A need for such an identification device also exists for pets. Even though identifying tags are commonly worn by pets, many pet owners find that it takes a considerable period of time to acquire new dog tags or to have etched name tags produced for their pets when old tags are lost. Such pet owners would like to be able to quickly and inexpensively provide an identification device which could be used during the period when the new conventional tags are being produced. In providing such an identification device for people or for animals, it would in many cases be desirable to provide the information in such a wa that it may not be readily viewed by a casual observer. For example, many women would be reluctant to have their names or addresses and telephone numbers prominently displayed on their person for obvious reasons.

OBJECTS OF THE INVENTION

It is an object of the present invention to provide an identification device which may be worn on a person's arm or leg to eliminate the need for carrying identification in a purse, billfold, etc.

It is another object of the present invention to provide an identification device which may be inscribed with personal information directly by the user using a conventional writing instrument such as a pen or pencil.

It is a further object of the present invention to provide an identification device which is capable of conveying information in an emergency situation but which does not provide viewable information under ordinary circumstances.

It is a further object of the present invention to provide an identification device which is readily adjustable to users of different size.

It is a further object of the present invention to provide an identification device which is relatively inexpensive to produce.

It is a further object of the present invention to provide an identification device which is rugged in construction and durable under harsh use conditions associated with athletic activities.

It is a further object of the present invention to provide an identification device which is attractive in appearance.

It is a further object of the present invention to provide an identification device which may be used with one or more other such devices in a loosely coupled relationship on a person's arm or leg.

It is a further object of the present invention to provide an identification device which is light in weight.

It is a further object of the present invention to provide an identification device which is comfortable to wear.

It is a further object of the present invention to provide an identification device which may be used to identify pets and which may worn about a pet's neck.

SUMMARY OF THE INVENTION

The present invention is directed to an identification and information conveying device which fulfills some or all of the foregoing objectives.

The present invention may comprise: an identification and personal information conveying device to be worn by a person comprising: (a) an elongate, flat, unitary, plastic member having a first end portion, a second end portion, and an intermediate portion and having a generally planar top surface and a generally planar bottom surface and having two parallel lateral side edges comprising a leading edge and a trailing edge and having opposite first and second end edges; (b) information receiving and displaying means fixedly attached to said bottom surface of said member for receiving and displaying information particular to a person wearing the device; (c) attachment means for attaching said first end portion of said device to said second end portion of said device for providing an annular configuration for positioning said device in encompassing relationship about a wearer's limb, said top surface of said member being positioned outwardly and said bottom surface of said member being positioned inwardly whereby information provided on said information receiving and display means is not readily viewable without removal of said device from the wearer.

The present invention may also comprise: an identification and personal information conveying device to be worn by a person comprising: an elongate, flat, unitary, plastic member having a first end portion, a second end portion, and an intermediate portion and having a generally planar top surface and a generally planar bottom surface and having two parallel lateral side edges comprising a leading edge and a trailing edge and having opposite first and second end edges; information receiving and displaying means fixedly attached to said bottom surface of said member for receiving and displaying information particular to a person wearing the device; wherein said information receiving and displaying means comprises means for receiving and displaying information transcribed thereon by a writing instrument such as a pen or pencil and wherein said information receiving and displaying means is adapted to maintain said transcribed information in readily readable form after exposure of said information displaying means to conditions associated with wearing of said device including perspiration and frictional contact with the wearer and wherein said information receiving and displaying means comprises hot stamped plastic film; fixed indicia associated with said information receiving and display device indicating the type of information to be provided by the wearer on said information receiving and display device; loose coupling means for enabling a plurality of said devices to be mounted in loosely coupled relationship on a person's limb; wherein said loose coupling means comprises a beveled surface portion on said top surface positioned adjacent said trailing edge and a beveled surface portion on said bottom surface positioned adjacent said leading edge, said beveled surface associated with said leading edge on one device being adapted to slide over and nest with said beveled surface associated with said trailing edge of another identical device when two of said devices are mounted in an annular configuration about a wearer's limb and wherein said elongate member end portions comprise linear configurations and wherein said elongate member intermediate portion comprises an arcuate configuration whereby said members comprise an asymmetrically shaped ring when attached about a wearer's limb whereby two of said devices are resistant to rotation relative to one another when positioned in loosely coupled relationship on a wearer's limb with an intermediate portion of one device positioned adjacent an intermediate portion of another device; attachment means for attaching said first end portion of said device to said second end portion of said device for providing an annular configuration for positioning said device in encompassing relationship about a wearer's limb, said top surface of said member being positioned outwardly and said bottom surface of said member being positioned inwardly whereby information provided on said information receiving and display means is not readily viewable without removal of said device from the wearer including a plurality of holes provided at a central portion of said first end portion of said member and a plurality of stud portions integrally formed with said member and extending outwardly from said top surface thereof on said second end portion thereof.

The present invention may also comprise: a method of providing a wearer with identification which is readily available in an emergency situation, but which is not ordinarily viewable, comprising the steps of: (a) providing a device comprising an elongate, flat, unitary, plastic member having a first end portion, a second end portion, and an intermediate portion and having a generally planar top surface and a generally planar bottom surface and having two parallel lateral side edges comprising a leading edge and a trailing edge and having opposite first and second end edges; information receiving and displaying means fixedly attached to said bottom surface of said member for receiving and displaying information particular to a wearer wearing the device; attachment means for attaching said first end portion of said device to said second end portion of said device for providing an annular configuration for positioning said device in encompassing relationship about a wearer's body part with said top surface of said member being positioned outwardly and said bottom surface of said member being positioned inwardly whereby information provided on said information receiving and display means is not readily viewable without removal of said device from the wearer; (b) providing information particular to a wearer on the information receiving and display means; (c) mounting the device around a wearer's body part with the information receiving and display means located in inwardly positioned nonviewable relationship.

The present invention may also comprise an identification and personal information conveying device to be worn by a pet comprising: (a) an elongate, flat, unitary, plastic member having a first end portion, a second end portion, and an intermediate portion and having a generally planar top surface and a generally planar bottom surface and having two parallel lateral side edges comprising a leading edge and a trailing edge and having opposite first and second end edges; (b) information receiving and displaying means fixedly attached to said bottom surface of said member at said intermediate portion thereof for receiving and displaying information particular to a pet wearing the device; (c) attachment means for attaching said first end portion of said device to said second end portion of said device for providing an annular configuration for positioning said device in encompassing relationship about a wearer's neck said top surface of said member being positioned outwardly and said bottom surface of said member being positioned inwardly whereby information provided on said information receiving and display means is not readily viewable without removal of said device from the wearer.

BRIEF DESCRIPTION OF THE DRAWINGS

An illustrative and presently preferred embodiment of the invention is shown in the accompanying drawing in which:

FIG. 1 is a top plan view of an identification and personal information conveying device.

FIG. 2 is a bottom plan view of the device of FIG. 1.

FIG. 3 is a left side elevation view of the device of FIG. 1.

FIG. 4 is a right side elevation view of the device of FIG. 1.

FIG. 5 is a front end elevation view of the device of FIG. 1.

FIG. 6 is a rear end elevation view of the device of FIG. 1.

FIG. 7 is perspective view illustrating the mounting of the device of FIGS. 1–6 about a person's wrist.

FIG. 8 is a perspective view illustrating the mounting of two devices of the type illustrated in FIGS. 1–7 about a person's wrist in a loosely coupled configuration.

FIG. 9 is a detail cross sectional view of two overlapping portions of two identical devices of the type illustrated in FIG. 8.

FIG. 10 is perspective view illustrating the mounting of an alternate embodiment of the device of FIGS. 1–9 about a dog's neck.

DETAILED DESCRIPTION OF THE INVENTION

The identification and personal information conveying device 10 of the present invention comprises an integrally formed, elongate, flat, flexible, elastic, plastic member 12. The member 12 may comprise a linearly extending first end portion 14, a linearly extending second end portion 16, and an intermediate arcuately extending portion 18 integrally connecting the first and second portions. The elongate member 12 comprises a generally flat top surface 20, FIG. 1, having a relatively large area planar surface portion 22 and a relatively small area beveled surface portion 24. Surfaces 22 and 24 interface at a line 23 extending parallel to a trailing edge 34 of the member. Member 12 also comprises a generally flat bottom surface 26, FIG. 2, comprising a relatively large area planar surface portion 28 which extends parallel to top surface portion 22 and a relatively small area beveled surface portion 30 which interface with surface 28 at a line 29 extending parallel to a leading edge 32 of the member. The beveled portions are preferable of identical taper. The member's leading edge 32 and trailing edge 34 extend in parallel relationship to one another and terminate at a first arcuately shaped end edge 36 and a second arcuately shaped end edge 38.

In one preferred embodiment of the invention, each end portion 14, 16 of member 12 may have a length of approximately 3.0 inches. The longitudinally extending distance of the intermediate portion 18 may be approximately 3.75 inches, and the radii of curvature of the intermediate portion may be approximately 3.07 inches and 2.98 inches at the leading edge 32 and trailing edge 34, respectively. The width of the elongate member 12 may be approximately 0.75 inches. The thickness of the member extending between the large area planar surface portions 22 and 28 may be approximately 0.05 inches, the thickness at the outer terminal edge of each beveled portion 24, 30 may be approximately 0.03 inches. Each end edge 36, 38 may comprise a radius of approximately 0.51 inches.

An information receiving and display means 40 is provided on the bottom surface 26 of the member 12. The information receiving and display means 40 may comprise a plurality of areas 42, 44, 46 adapted to be written upon by a user of the device. In one preferred embodiment, these areas 42, 44, 46 are provided by a plastic film which is hot stamped onto the bottom surface 26 of the member 12. The plastic film used to provide areas 42, 44, 46 may of a type such as is commonly used for providing a signature area on credit cards. The hot stamping process for applying the plastic film to member 12 may also be similar or identical to that used for applying a plastic film signature area to credit cards. Hot stamped plastic film may also be used to provide preprinted matter 48 which indicates what type of information is to be provided in the areas 42, 44, 46 by a particular user of the device. Information 50 which is particular to the user of the device may thus be applied in the areas 42, 44, 46 by pen, pencil, or other conventional marking means. Thus, the information receiving and display means 40 of the present invention allows a future user of the device to mark the device himself or herself immediately after acquisition thereof, thereby enabling the device to be used immediately and avoiding any inconvenience associated with having a manufacturer or vender provide the information particular to the user.

Adjustable attachment means 52, FIGS. 1 and 2, are integrally formed in the elongate member 12, enabling the member 12 to be adjustably attached in a loop configuration about a person's wrist, as illustrated in FIGS. 7 and 8. In one preferred embodiment of the invention, the adjustable attachment means comprises a plurality of holes 54, 56, 58, 60, provided in end portion 16 of the elongate member, which are adapted to mate with a plurality of studs 62, 64, 66, 67 provided in the opposite end portion 14 of the member. Each stud may comprise a relatively smaller diameter portion 68, FIG. 6, having a diameter slightly smaller than the diameter of holes 54, 56, 58, 60 and having an axial length slightly longer than the thickness of the member 12. Each stud may further comprise a relatively larger diameter portion 70 having a diameter slightly larger than the diameter of hole 54, 56, 58, 60. The plastic material from which the member 12 is constructed is sufficiently resilient to allow penetration of the relatively larger diameter portion through the holes when thus urged by a person snapping the device about his wrist. The plastic material of member 12 is sufficiently stiff to prevent the relatively larger diameter portion 70 from slipping back through the holes during normal wearing conditions.

The adjustable attachment means 52 may further comprise arcuate shaped indentations 72, 74, FIG. 2, provided on bottom surface 28 and positioned approximately on inch from associated end edges 36, 38, respectively. Each indentation may be, e.g., 0.020 inches wide and 0.005 inches deep and may have a shape identical to an associated end edge. The arcuate shaped indentations provide a cutting line which a person may follow with an ordinary pair of sewing scissors to shorten the member 12, adapting it for use by children.

FIG. 7 illustrates a typical use of the identification and personal information conveying device 10. It will be seen from FIG. 7 that the first end portion 14 of the device is snappingly engaged with the second end portion 16 with top surface 20 of the device positioned outwardly such that bottom surface 26 and information receiving and display means 40 are positioned in unexposed relationship adjacent to the person's body surface.

FIGS. 8 and 9 illustrate the use of two identical devices 10 and 10′ positioned in loosely coupled relationship with the intermediate portions 18, 18′ thereof positioned in adjacent parallel relationship with the beveled bottom surface portion 30 associated with the leading edge 32 of the trailingly positioned device 10 positioned in overlapping relationship with the beveled portion 24′ associated with the trailing edge 34′ of the leadingly positioned device 10′. The arcuate shapes of intermediate portions 18, 18′ prevent relative rotational movement between the two devices 10, 10′, and the overlapping relationship of the associated bevel portions 30, 24′ of the two devices 10, 10′ provide a nesting arrangement between the two devices which provides an attractive appearance on the wearer's wrist. FIG. 9 illustrates an embodiment of the invention in which the beveled areas 24′, 30 are provided with a taper extending to a zero thickness at the associated edges.

As illustrated in FIG. 10, in another embodiment of the invention, an identification and personal information conveying device 10A may be used to provide identification and other information for an animal such as a dog. In this embodiment of the invention, the device 10A is adapted for wearing about an animal's neck. The device 10A may be identical to the device 10 described with reference to FIGS. 1–6. However, in one preferred embodiment as illustrated in FIG. 10, the device 10A is different than device 10 in that it comprises a completely linear shape in which the intermediate portion of the device is linear rather than arcuate whereby a uniform circular configuration is provided when the member is snapped into place about the animal's neck. The information receiving and display means used with device 10A may be provided with preprinted matter such as at 48 in FIG. 2 but which indicates information to be provided which is suitably adapted for an animal such as by providing a space for the owner's name, the animal's kennel number, veterinarian, etc. In one preferred embodiment of the device 10A for use by animals, elongate plastic member 12A is impregnated with a chemical adapted to repel insects such as fleas and ticks. A chemical commonly used in commercially available flea and tick collars may be used for this purpose.

It is contemplated that the inventive concepts herein described may be variously otherwise embodied and it is intended that the appended claims be construed to include alternative embodiments of the invention except insofar as limited by the prior art.

What is claimed is:

1. An identification and personal information conveying device to be worn by a person comprising:
    an elongate, flat, unitary, plastic member having a first end portion, a second end portion, and an intermediate portion and having a generally planar top surface and a generally planar bottom surface and having two parallel lateral side edges comprising a leading edge and a trailing edge and having opposite first and second end edges;
    information receiving and displaying means fixedly attached to said bottom surface of said member for receiving and displaying information particular to a person wearing the device;
    wherein said information receiving and displaying means comprises means for receiving and displaying information transcribed thereon by a writing instrument such as a pen or pencil and wherein said information receiving and displaying means is adapted to maintain said transcribed information in readily readable form after exposure of said information displaying means to conditions associated with wearing of said device including perspiration and frictional contact with the wearer and wherein said information receiving and displaying means comprises hot stamped plastic film whereby a wearer of the device is enabled to transcribe information on said information receiving and display means with a pen or pencil immediately after acquisition of the device, whereby the device is immediately rendered functional and whereby the need for special tools and/or resort to complex or time consuming processes for providing said information is obviated;
    fixed indicia associated with said information receiving and display device indicating the type of information to be provided by the wearer on said information receiving and display means;
    loose coupling means for enabling a plurality of said devices to be mounted in loosely coupled relationship on a wearer's limb;
    wherein said loose coupling means comprises a beveled surface portion on said top surface positioned adjacent said trailing edge and a beveled surface portion on said bottom surface positioned adjacent said leading edge, said beveled surface associated with said leading edge on one device being adapted to slide over and nest with said beveled surface associated with said trailing edge of another identical device when two of said devices are mounted in an annular configuration about a wearer's limb and wherein said elongate member end portions comprise linear configurations and wherein said elongate member intermediate portion comprises an arcuate configuration whereby said members comprise an asymmetrically shaped ring when attached about a wearer's limb whereby two of said devices are resistant to rotation relative to one another when positioned in loosely coupled relationship on a wearer's limb with an intermediate portion of one device positioned adjacent an intermediate portion of another device;
    nondestructably releasable attachment means for attaching said first end portion of said device to said second end portion of said device for providing an annular configuration for positioning said device in encompassing relationship about a wearer's limb with said top surface of said member being positioned outwardly and said bottom surface of said member being positioned inwardly whereby information provided on said information receiving and display means is not readily viewable without removal of said device from the wearer, including a plurality of holes provided at a central portion of said first end portion of said member and a plurality of stud portions integrally formed with said member and extending outwardly from said top surface thereof on said second end portion thereof.

2. A method of providing a wearer with identification which is readily available in an emergency situation, but which is not ordinarily viewable, comprising the steps of:
    (a) providing a device comprising an elongate, flat, unitary, plastic member having a first end portion, a second end portion, and an intermediate portion and having a generally planar top surface and a generally planar bottom surface and having two parallel lateral side edges comprising a leading edge and a trailing edge and having opposite first and second end edges; information receiving and displaying means fixedly attached to said bottom surface of said member at said intermediate portion thereof for receiving and displaying information particular to a wearer wearing the device; attachment means for attaching said first end portion of said device to said second end portion of said device for providing an annular configuration for positioning said device in encompassing relationship about a wearer's body part with said top surface of said member being positioned outwardly and said bottom surface of said member being positioned inwardly whereby information provided on said information receiving and display means is not readily viewable without removal of said device from the wearer;
    (b) providing information particular to a wearer on the information receiving and display means;
    (c) mounting the device around a wearer's body part with the information receiving and display means located in inwardly positioned nonviewable relationship.

3. An identification and personal information conveying device to be worn by a person comprising:

an elongate, flat, unitary, plastic member having a first end portion, a second end portion, and an intermediate portion and having a generally planar top surface and a generally planar bottom surface and having two parallel lateral side edges comprising a leading edge and a trailing edge and having opposite first and second end edges;

information receiving and displaying means fixedly attached to said bottom surface of said member for receiving and displaying information particular to a person wearing the device;

wherein said information receiving and displaying means comprises means for receiving and displaying information transcribed thereon by a writing instrument such as a pen or pencil and wherein said information receiving and displaying means is adapted to maintain said transcribed information in readily readable form after exposure of said information displaying means to conditions associated with wearing of said device including perspiration and frictional contact with the wearer and wherein said information receiving and displaying means comprises hot stamped plastic film;

nondestructably releasable attachment means for attaching said first end portion of said device to said second end portion of said device for providing an annular configuration for positioning said device in encompassing relationship about a wearer's limb, said top surface of said member being positioned outwardly and said bottom surface of said member being positioned inwardly whereby information provided on said information receiving and display means is not readily viewable without removal of said device from the wearer.

4. The invention of claim 3 further comprising fixed indicia associated with said information receiving and display device indicating the type of information to be provided by the wearer on said information receiving and display device.

5. The invention of claim 3 wherein said device further comprises loose coupling means for enabling a plurality of said devices to be mounted in loosely coupled relationship on a wearer's limb.

6. The invention of claim 5 wherein said loose coupling means comprises a beveled surface portion on said top surface positioned adjacent said trailing edge and a beveled surface portion on said bottom surface positioned adjacent said leading edge, said beveled surface associated with said leading edge on one device being adapted to slide over and nest with said beveled surface associated with said trailing edge of another identical device when two of said devices are mounted in an annular configuration about a wearer's limb.

7. The invention of claim 6 wherein said elongate member end portions comprise linear configurations and wherein said elongate member intermediate portion comprises an arcuate configuration whereby said members comprise an asymmetrically shaped ring when attached about a wearer's limb whereby said devices are resistant to rotation relative to one another when positioned in loosely coupled relationship on a wearer's limb with an intermediate portion of one device positioned adjacent an intermediate portion of another device.

8. The invention of claim 3 wherein said attachment means comprises:
a plurality of holes provided at a central portion of said first end portion of said member; and
a plurality of stud portions integrally formed with said member and extending outwardly from said top surface thereof on said second end portion thereof.

9. An identification and personal information conveying device to be worn by a pet comprising:

an elongate, flat, unitary, plastic member having a first end portion, a second end portion, and an intermediate portion and having a generally planar top surface and a generally planar bottom surface and having two parallel lateral side edges comprising a leading edge and a trailing edge and having opposite first and second end edges;

information receiving and displaying means fixedly attached to said bottom surface of said member for receiving and displaying information particular to a pet wearing the device;

wherein said information receiving and displaying means comprises means for receiving and displaying information transcribed thereon by a writing instrument such as a pen or pencil and wherein said information receiving and displaying means is adapted to maintain said transcribed information in readily readable form after exposure of said information displaying means to conditions associated with wearing of said device including perspiration and frictional contact with the wearer and wherein said information receiving and displaying means comprises hot stamped plastic film;

nondestructably releasable attachment means for attaching said first end portion of said device to said second end portion of said device for providing an annular configuration for positioning said device in encompassing relationship about a wearer's body portion, said top surface of said member being positioned outwardly and said bottom surface of said member being positioned inwardly whereby information provided on said information receiving and display means is not readily viewable without removal of said device from the wearer.

10. The invention of claim 9 wherein said elongate member is impregnated with an insect repelling chemical.

11. The invention of claim 9 wherein said attachment means comprises an adjustable attachment means for enabling the diameter of said annular configuration to be varied.

12. The invention of claim 11 wherein said attachment means comprises:
a plurality of holes provided at a central portion of said first end portion of said member; and
a plurality of stud portions integrally formed with said member and extending outwardly from said top surface thereof on said second end portion thereof.

* * * * *